United States Patent [19]

Holter

[11] Patent Number: 4,621,654

[45] Date of Patent: Nov. 11, 1986

[54] ATTITUDE AND PRESSURE RESPONSIVE VALVE

[76] Inventor: John W. Holter, Valley Forge Towers South 619, King of Prussia, Pa. 19405

[21] Appl. No.: 825,532

[22] Filed: Feb. 3, 1986

[51] Int. Cl.⁴ .............................................. A61M 27/00
[52] U.S. Cl. ....................................... 137/38; 137/512; 137/848; 417/478; 604/10; 604/185
[58] Field of Search .................. 137/38, 512, 848, 849; 417/478; 604/9, 10, 129, 185

[56] References Cited

U.S. PATENT DOCUMENTS

| | | | |
|---|---|---|---|
| 1,352,650 | 9/1920 | Blanchard | 137/38 |
| 2,969,066 | 1/1961 | Holter | 604/9 |
| 3,566,875 | 3/1971 | Stoehr | 604/9 |
| 3,889,687 | 6/1975 | Harris | 604/10 |
| 3,985,140 | 10/1976 | Harris | 604/9 |

*Primary Examiner*—Robert G. Nilson
*Attorney, Agent, or Firm*—Richard D. Weber

[57] ABSTRACT

A valve assembly for relieving intracraneal pressure includes a valve housing adapted for implantation and having an inlet port for connection to a ventricular catheter and an outlet port for connection to a venus or peritoneal catheter. The valve housing includes a fluid passage, the flow through which is controlled by a first pressure responsive valve of relatively high resistance and a second pressure responsive valve of relatively low resistance spaced downstream of said first pressure responsive valve. An attitude responsive valve is disposed in said fluid passage in parallel with said first pressure responsive valve. The valve assembly is implanted in a patient with the attitude responsive valve in a closed position when the patient is in an upright position and in an open position when the patient is in a horizontal position. The employment of pressure responsive and attitude responsive valves in parallel provides ventricular pressure relief regardless of the patient's position.

10 Claims, 9 Drawing Figures

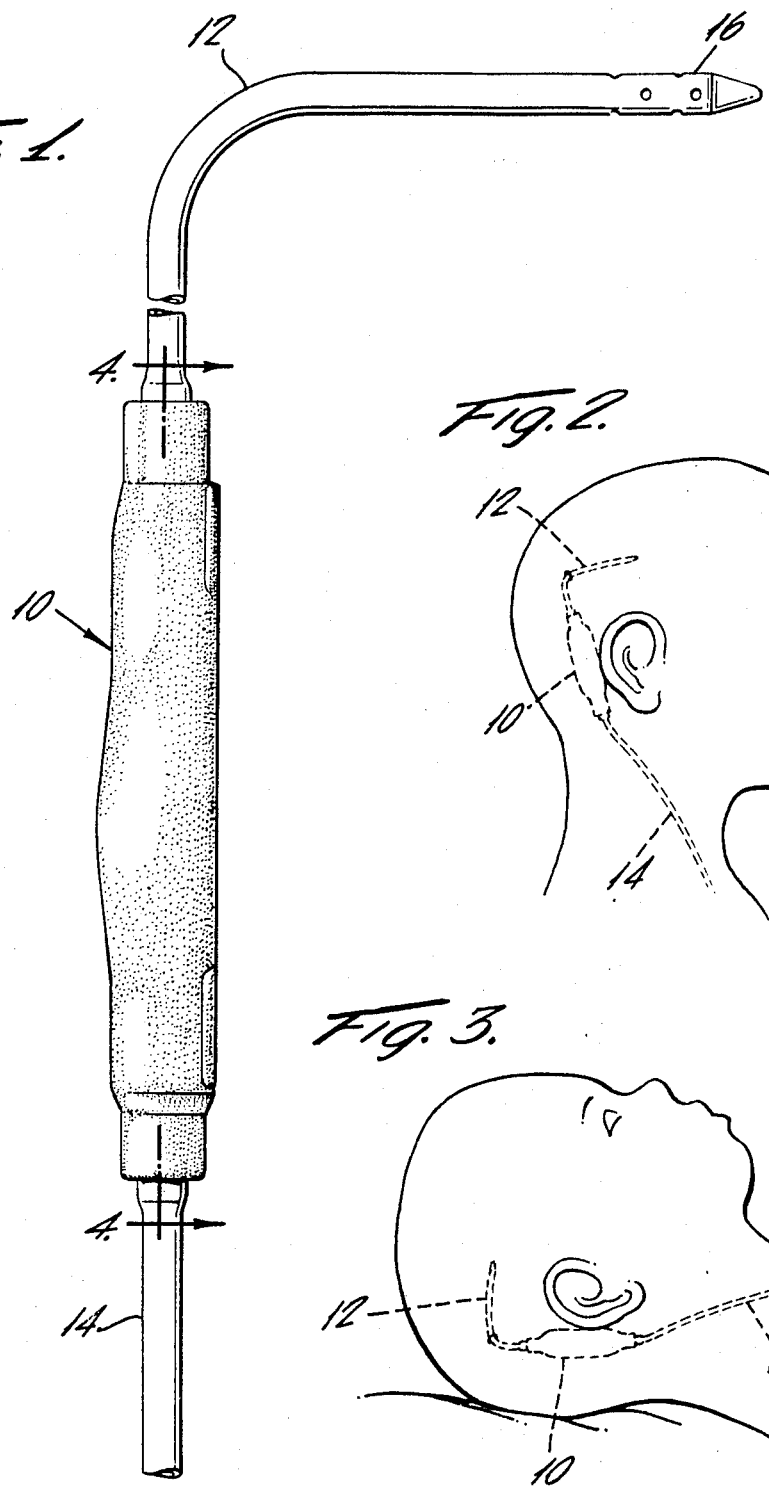

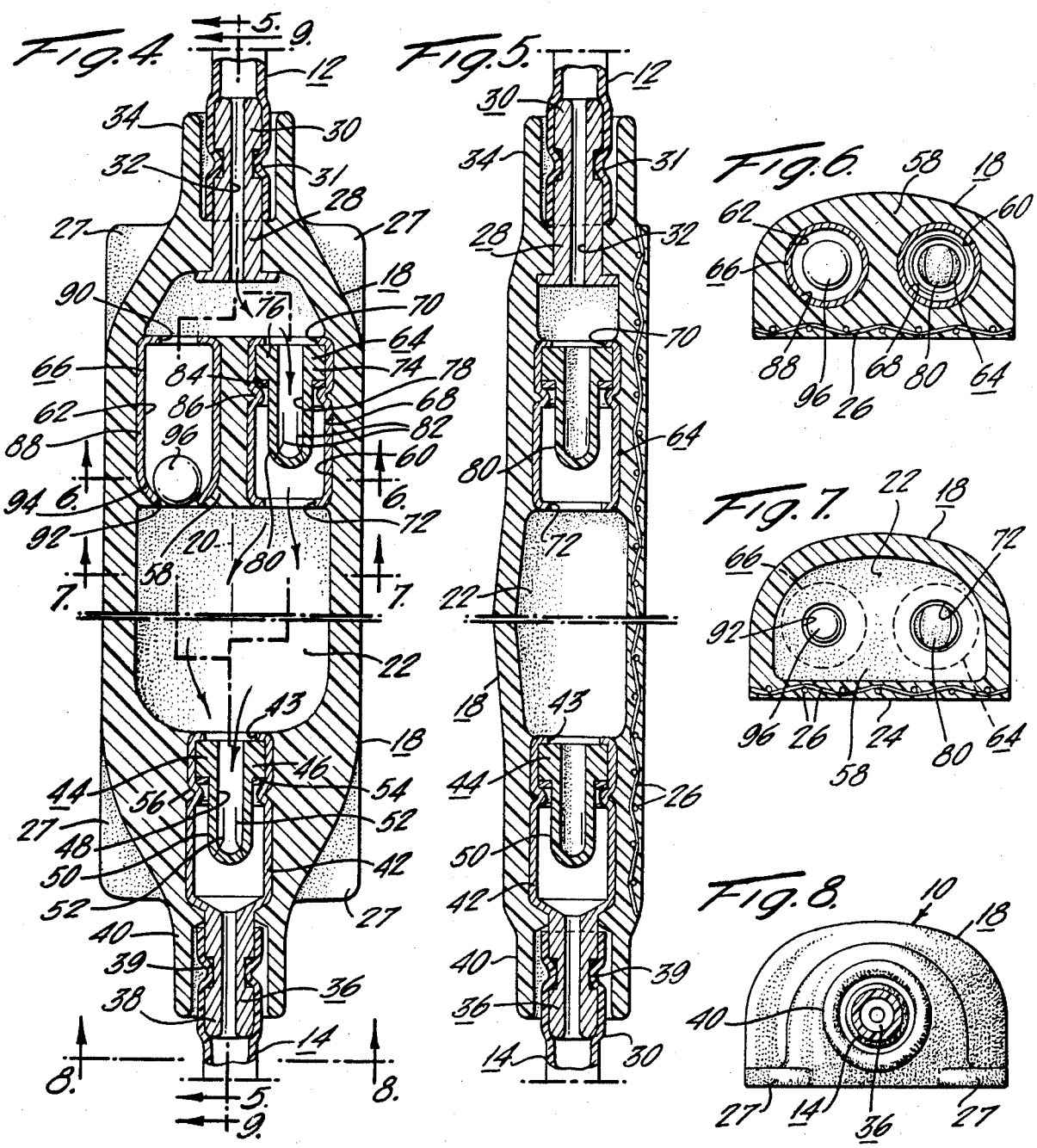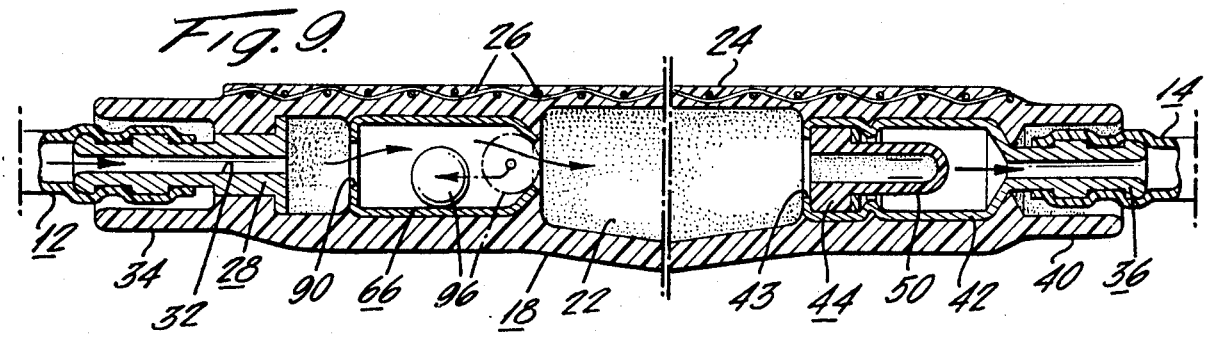

4,621,654

ATTITUDE AND PRESSURE RESPONSIVE VALVE

BACKGROUND OF THE INVENTION

The present invention relates generally to a valve for providing pressure relief in response both to attitude and pressure conditions, and relates more particularly to such a valve adapted for implantation to relieve intracraneal pressure in treatment of hydrocephalus.

Devices for draining ventricular fluid in cases of hydrocephalus have been available for some time. An early example of such a device is shown in my U.S. Pat. No. 2,969,066, issued Jan. 24, 1961. These devices essentially are pressure responsive valves which open upon the occurrence of a predetermined gradient across the valve to allow flow of cerebrospinal fluid sufficient to lower the ventricular pressure to the desired level.

Since the typical cerebrospinal fluid shunt valve responds only to the fluid pressure gradient, such valves are unable to accommodate changes in attitude of the patient if the valve discharges into a catheter of considerable length such as a peritoneal catheter, since the pressure at the upper end of the catheter into which the valve discharges in a pressure gradient responsive valve controls the actual pressure relief achieved. Accordingly, such a valve implanted in a patient's head and utilizing a lengthy peritoneal catheter would function normally only when the patient were in an upright position, but would not produce the desired relief when the patient were in the horizontal position because of the substantial increase in the pressure at the discharge port of the valve.

SUMMARY OF THE INVENTION

The present invention overcomes the above shortcoming of prior art shunt valves by providing a valve assembly which is responsive both to attitude and pressure. This is accomplished by a parallel arrangement of a pressure responsive valve and an attitude responsive valve, thus providing an alternate flow path dependent upon the patient's attitude. The pressure responsive valve is designed to open under a relatively high pressure gradient, while the attitude responsive valve will open when the patient is in a substantially horizontal position. A second pressure responsive valve opening under a relatively low pressure gradient is provided at the outlet of the valve assembly, primarily to guard against fluid backflow.

It is accordingly a first object of the invention to provide a shunt valve for treatment of hydrocephalus which is both pressure responsive and attitude responsive to provide relief of intracraneal pressure regardless of the attitude of the patient and the length of the catheter into which the valve discharges.

A further object of the invention is to provide a valve as described of a relatively simple construction which can readily be miniaturized, and which can be fabricated of materials suitable for implantation.

Additional objects and advantages of the invention will be more readily apparent from the following description of a preferred embodiment thereof.

BRIEF DESCRIPTION OF THE DRAWINGS

FIG. 1 is a side elevational view of a valve assembly in accordance with the invention connected at its upper end with a ventricle catheter and at its lower end to a partially illustrated venous or peritoneal catheter;

FIG. 2 is a schematic elevational view showing the assembly of FIG. 1 implanted in a patient's head;

FIG. 3 is a view similar to FIG. 2, but showing the patient in a reclining position;

FIG. 4 is an enlarged sectional view taken along line 4—4 of FIG. 1 and showing interior details of the valve assembly;

FIG. 5 is a sectional view taken along line 5—5 of FIG. 4;

FIG. 6 is a sectional view taken along line 6—6 of FIG. 4;

FIG. 7 is a sectional view taken along line 7—7 of FIG. 4;

FIG. 8 is a view partly in section taken along line 8—8 of FIG. 4; and

FIG. 9 is a sectional view taken along line 9—9 of FIG. 4 with the valve assembly in a horizontal position, showing in dot/dash lines the closed position of the attitude actuated valve.

DESCRIPTION OF THE PREFERRED EMBODIMENT

Referring to the drawings and particularly FIGS. 1-3 thereof, a valve assembly 10 in accordance with the present invention is shown connected at its upper end with a ventricular catheter 12 and at its lower end with a venous or peritoneal catheter 14. The valve assembly and attached catheters are adapted for placement beneath the skin of a hydrocephalitic patient in the position generally shown in FIG. 2 with the perforated distal end 16 of the ventricle catheter being appropriately located in a region of accumulated cerebrospinal fluid to provide fluid pressure relief as required. The fluid drained by the ventricle catheter 12 as regulated by the valve assembly 10 passes through the catheter 14 preferably into the peritoneal cavity of the patient or, alternately into the venous system. Although the valve assembly is conventionally placed behind the mastoid prominence as illustrated, when used with a peritoneal catheter it may alternately be located in the chest region. This latter location minimizes the risk of infection in the brain area, especially should complications arise requiring a repositioning, reattachment or replacement of the assembly.

Since valve assemblies for relieving ventricular pressure are typically of the type opening in response to the relative pressure between the ventricular catheter and the peritoneal or venous catheter, a markedly different relief function is provided when the patient's position changes from an upright to a reclining attitude due to a change in pressure at the outlet end of the valve assembly. For example, in FIG. 2 with the patient's upper body in an upright position such as when sitting or standing, the valve outlet pressure will be relatively low since the fluid column within the lower catheter will be in an essentially vertical attitude. In contrast, when the patient is in a reclining position as in FIG. 3, the pressure at the valve outlet will be significantly higher since the fluid in the peritoneal or venous catheter will be substantially horizontal.

As a result, since the valve assembly components are normally selected to effect the desired pressure relief function when the patient is in the upright position of FIG. 2, the desired relief function cannot be obtained when the patient is in the reclining position of FIG. 3 since the downstream catheter pressure will be substantially higher. The conventional type of valve would accordingly permit excessive ventricle pressure buildup when the patient is in the reclining position. If the valve were chosen to provide the appropriate pressure responsive opening when the patient were in the reclining position of FIG. 3, such a valve would produce excessive fluid drainage in the upright position of FIG. 2 with potentially serious results.

The present valve assembly 10 overcomes this shortcoming of conventional pressure responsive valves by incorporating therewithin an attitude responsive valve which will open only when the patient is in a reclining position. By employing the attitude responsive valve in the valve in parallel with the pressure responsive valve, appropriate pressure relief is attained regardless of the patient's position.

The details of the present valve assembly 10 are shown in FIGS. 4-9 and include a resilient elongated valve housing 18 having a longitudinal axis 20. The housing 18 is hollow, with the walls thereof defining a fluid chamber 22 extending most of the length of the housing. Both the housing 18 and the fluid chamber 22 as shown in FIG. 7 are in section of a D-shape, one wall 24 of the housing being essentially planar and incorporating therewithin a fabric reinforcement layer 26. The fabric reinforced wall 24 extends at the four corners of the housing to form ear portions 27 which facilitate the anchoring of the valve assembly in place such as by means of ligatures.

In order to permit fluid passage into the housing 22, a tubing connector 28 is molded into one end of the housing, preferably in alignment with the longitudinal housing axis 20. The tubing connector 28 includes an outwardly extending portion 30 over which the proximal end of the ventricular catheter is disposed. An annular groove 31 in the connector portion 30 permits a peripheral constriction of the catheter such as by suture material (not shown) to provide a locking of the catheter to the connector and hence the housing. An axial passage 32 in the connector permits fluid flow from the catheter into the chamber 22. The end of the housing terminates in a collar portion 34 which protects the catheter connection from dislodging influences.

A similar tubing connector 36 is provided at the opposite end of the housing 18, the connector 36 including ribs 38 over which the proximal end of the peritoneal catheter 14 is secured. A collar portion 40 of the housing 18 extends around the extending connector 36 to protect the attachment of the catheter 14.

The connector 36 as illustrated is preferably formed as an integral part of a hollow valve casing 42 molded within the lower end of the housing 18 and within which is disposed a pressure responsive valve 44. An opening 43 in the casing 42 provides fluid communication from the chamber 22 into the casing 42 as controlled by the valve 44. The valve 44 opens in response to a relatively low pressure differential between the fluid in the chamber 22 and that within the upper end of the catheter 14.

The construction of the low pressure responsive valve 44 may be of a variety of types but is preferably as illustrated of a type comprising a valve body 46 of an elastic material having a central valve bore 48. The valve is of a diameter sufficient to fill the casing 42 at its upper end, but is narrowed into an elongated closed barrel portion 50 at its lower end. A pair of slits 52 in the closed end of the barrel portion permit expansion deformation of the end of the barrel portion and a flow of fluid through the slits upon the occurrence of a predetermined pressure differential between the fluid within the valve bore 48 and the hollow valve casing 42. The valve body 46 is retained in position at the upper end of the valve casing 42 by means of a retaining ring 54 cooperating with an annular rib 56 of the valve casing 42.

The chamber 22 is divided by a bulkhead 58 disposed relatively close to the chamber inlet. The bulkhead includes a pair of parallel bores 60 and 62 parallel with the longitudinal axis of the valve assembly and adapted respectively to receive a high pressure responsive valve assembly 64 and an attitude responsive valve assembly 66.

The high pressure responsive valve assembly 64, which is in structure identical with the low pressure responsive valve 44, includes a hollow valve casing 68 having an upper opening 70 and a lower opening 72 therein. A valve element 74 within the casing 68 includes a valve body 76 having a bore 78 therein. A reduced diameter barrel portion 80 of the valve element 74 includes a pair of slits 82 therein which, upon the occurrence of a predetermined pressure differential between the fluid present in the bore 78 and the casing 68, opens in response to elastic deformation of the valve barrel portion. A retaining ring 84 cooperates with the annular rib 86 of the casing 68 to secure the valve element 74 in place against the upper end of the casing 68.

The attitude responsive valve 66 includes a hollow cylindrical valve casing 88 having an upper inlet opening 90 and a lower outlet opening 92 therein to permit fluid passage therethrough. The casing 88 adjacent the outlet opening 92 is of a frusto-conical configuration to serve as a seat for a valve ball 96 which has a diameter less than the diameter of the casing 88 but greater than that of the opening 92. The ball 96 will accordingly be guided by the frusto-conical portion 94 of the casing to seat directly over and seal the outlet opening 92 when the valve assembly is in a vertical attitude as shown in FIG. 4, but will roll under the force of gravity away from the opening 92 when the valve assembly is in a horizontal attitude as shown in FIG. 9.

The high pressure responsive valve 64 is calibrated to require a substantial pressure differential to open, for example 180 mm H₂O. The low pressure responsive outlet valve 44, in contrast, should require only a small pressure differential to open, for example 10-20 mm H₂O. The outet valve 44 is required principally to prevent possible back flow into the chamber 22. The outlet valve 44 additionally permits use of the lower portion of chamber 22 as a pumping chamber to test the operability of the implanted valve and catheter system.

The operation of the valve assembly is automatic and provides a predetermined pressure relief to the cranial ventricles regardless of the patient's attitude. As indicated above, the valve assembly is implanted so as to be in a substantially vertical attitude when the patient is in an upright position, as shown in FIG. 2. The perforated distal end 16 of the ventricle catheter is located in the appropriate cavity to drain the cerebrospinal fluid as required to maintain the desired fluid pressure. The venous or peritoneal catheter 14 is similarly implanted in a well known manner to provide a flow path of drained fluid to the selected body region.

Since the entire fluid drainage system including the ventricle catheter 12, the valve assembly 10 and the venous or peritoneal catheter 14 is at all times filled with fluid, it forms a fluid column of substantial length which in the absence of appropriate valve resistance, could, especially in the case of a peritoneal catheter, reduce the ventricle pressure to an undesireably low pressure. Accordingly, the high pressure responsive valve 64 is chosen with a substantial pressure differential resistance and will normally operate only when the patient is in the substantially upright position, at which position the pressure at the upper end of the catheter 14 is minimized and the pressure differential across the valve is greatest.

When the patient assumes a horizontal position, the ball 96 as illustrated in FIG. 9 falls away from the opening 92, thereby opening a flow path through the valve casing 88 bypassing the pressure responsive valve 64. The opening of either the pressure responsive valve 64 or the attitude sensitive valve 66 will normally be sufficient to simultaneously open the outlet valve 44 and permit a fluid flow into the catheter 14.

The portion of the chamber 22 downstream of the bulkhead 58 may be utilized as a pumping chamber to test the operability of the valves in the manner described in the above-mentioned U.S. Pat. No. 2,969,066. Since the implantation is just beneath the skin, this portion of the chamber may be manually compressed to force fluid within the chamber through the outlet valve.

The portion of chamber 22 upstream of the bulkhead 58 may be utilized as a convenient injection cavity for introduction of medication or for monitoring the pressure being maintained by the valve assembly.

The elastic portions of the valve assembly including the valve housing, bulkhead and the elastic pressure responsive valves are preferably made of a rubber like material such as Silastic or other elastomeric polymer suitable for implantation. The rigid elements including the several valve casings and the tubing connectors are preferably made of type 316 stainless steel or other suitable metal. The ball 96 may also be made of a heavy metal such as stainless steel although it may be advantageous to employ a precious metal such as gold to maximize the weight and hence the gravity force serving to operate this element.

Although the pressure responsive valve type illustrated and described is preferred, other types of pressure actuated valves may also be employed, including but not limited to miter or fishmouth valves, ball type valves, or flap type valves.

The attitude responsive valve should be a gravity actuated valve and is preferably of the free floating ball type as illustrated and described. A modified form of attitude responsive valve could comprise a very thin flow activated membrane or flap valve which would close when the patient stood up or sat up as a sudden increase of fluid flow would serve to close such a flap valve.

Manifestly, changes in details of construction can be effected by those skilled in the art without departing from the invention.

I claim:

1. An attitude and pressure responsive valve assembly comprising:
    an elongated hollow housing defining a fluid chamber therewithin,
    a fluid inlet port in one end of said housing,
    a fluid outlet port in the opposite end of said housing from said fluid inlet port,
    a first pressure responsive valve and an attitude responsive valve disposed in parallel and defining alternate flow paths within said fluid chamber for fluid flowing from said inlet port through said chamber to said outlet port,
    a second pressure responsive valve connecting said fluid chamber with said outlet port,
    said first pressure responsive valve requiring a substantially greater fluid pressure for opening than said second pressure responsive valve.

2. The invention as claimed in claim 1 wherein said pressure responsive valves are of the type responsive to the pressure gradient across said valves.

3. The invention as claimed in claim 1 wherein said attitude responsive valve comprises a ball valve including a freely floating ball.

4. The invention as claimed in claim 1 wherein said housing is formed of an elastic material permitting manual deformation of the housing chamber downstream of said first pressure responsive valve and attitude responsive valve to permit testing of the operability of the valve assembly.

5. A shunt valve for draining cerebrospinal fluid comprising:
    an elastomeric elongated hollow valve housing defining a fluid chamber therewithin,
    an inlet port at one end of said housing, means on said housing for connecting said inlet port with a ventricular catheter,
    an outlet port at the opposite end of said housing, means on said housing for connecting said outlet port with a drainage catheter,
    a bulkhead in said chamber dividing said chamber into upstream and downstream portions respectively communicating with said inlet and said outlet ports,
    a first port in said bulkhead having a pressure responsive valve disposed therein for controlling fluid passage from said upstream to said downstream chamber portion,
    a second port in said bulkhead having an attitude responsive valve disposed therein for providing an alternate controlled fluid passage from said upstream to said downstream chamber portion,
    a pressure responsive outlet valve controlling fluid flow from said downstream chamber portion into said outlet port,
    said pressure responsive valve in said bulkhead requiring a substantially greater pressure gradient for opening than said pressure responsive outlet valve.

6. The invention as claimed in claim 5 wherein said pressure responsive valves are of the type responsive to the pressure gradient across said valves.

7. The invention as claimed in claim 5 wherein said attitude responsive valve comprises a ball valve including a freely floating ball.

8. The invention as claimed in claim 7 wherein said ball valve includes a casing for said ball comprising a frustoconical portion having an opening therein smaller than the diameter of said ball, which opening is sealed by the ball when the casing is disposed with the opening at the bottom thereof.

9. The invention as claimed in claim 5 wherein said pressure responsive valves each comprise an elastomeric body portion having a closed bore therein with slits at the end of said bore which open upon elastic deformation of the valve body to permit fluid flow therethrough.

10. The invention as claimed in claim 5 wherein said downstream chamber portion is of a sufficient size to permit manual compression thereof when implanted in a patient to permit testing of the operability of the valve.

* * * * *